(12) United States Patent
Traber et al.

(10) Patent No.: US 8,828,971 B2
(45) Date of Patent: Sep. 9, 2014

(54) GALACTOSE-PRONGED CARBOHYDRATE COMPOUNDS FOR THE TREATMENT OF DIABETIC NEPHROPATHY AND ASSOCIATED DISORDERS

(71) Applicant: Galectin Therapeutics, Inc., Norcross, GA (US)

(72) Inventors: Peter G. Traber, Norcros, GA (US); Eliezer Zomer, Newton, MA (US)

(73) Assignee: Galectin Therapeutics, Inc., Norcross, GA (US)

( * ) Notice: Subject to any disclaimer, the term of this patent is extended or adjusted under 35 U.S.C. 154(b) by 0 days.

(21) Appl. No.: 13/998,197

(22) Filed: Oct. 10, 2013

(65) Prior Publication Data

US 2014/0099319 A1    Apr. 10, 2014

Related U.S. Application Data

(60) Provisional application No. 61/711,929, filed on Oct. 10, 2012.

(51) Int. Cl.
| | | |
|---|---|---|
| *A01N 43/04* | (2006.01) | |
| *A61K 31/715* | (2006.01) | |
| *A61K 38/02* | (2006.01) | |
| *C08B 37/00* | (2006.01) | |
| *A61K 31/7105* | (2006.01) | |
| *A61K 45/06* | (2006.01) | |

(52) U.S. Cl.
CPC ............ *C08B 37/006* (2013.01); *A61K 31/715* (2013.01); *A61K 38/02* (2013.01); *A61K 31/7105* (2013.01); *A61K 45/06* (2013.01)
USPC .............................................. 514/54; 514/62

(58) Field of Classification Search
None
See application file for complete search history.

(56) References Cited

U.S. PATENT DOCUMENTS

| | | | |
|---|---|---|---|
| 2,132,577 A | 10/1938 | Olsen et al. | |
| 2,444,266 A | 6/1948 | Maclay et al. | |
| 2,503,258 A | 4/1950 | Graham et al. | |
| 4,016,351 A | 4/1977 | Eschinasi et al. | |
| 4,268,533 A | 5/1981 | Williams et al. | |
| 4,686,106 A | 8/1987 | Ehrlich et al. | |
| 5,071,970 A | 12/1991 | le Grand et al. | |
| 5,498,702 A | 3/1996 | Mitchell et al. | |
| 5,681,923 A | 10/1997 | Platt | |
| 5,834,442 A | 11/1998 | Raz et al. | |
| 5,895,784 A | 4/1999 | Raz et al. | |
| 6,417,173 B1 | 7/2002 | Roufa et al. | |
| 6,423,314 B2 | 7/2002 | Platt et al. | |
| 6,444,655 B1 | 9/2002 | Nilsson | |
| 6,500,807 B1 | 12/2002 | Platt et al. | |
| 6,573,245 B1 | 6/2003 | Marciani | |
| 6,632,097 B2 | 10/2003 | Chang et al. | |
| 6,645,946 B1 | 11/2003 | Klyosov et al. | |
| 6,680,306 B2 | 1/2004 | Chang et al. | |
| 6,756,362 B2 | 6/2004 | Roufa et al. | |
| 6,770,622 B2 | 8/2004 | Jarvis et al. | |
| 6,890,906 B2 | 5/2005 | Chang et al. | |
| 6,914,055 B2 | 7/2005 | Klyosov et al. | |
| 6,982,255 B2 | 1/2006 | Klyosov et al. | |
| 7,012,068 B2 | 3/2006 | Klyosov et al. | |
| 7,230,096 B2 | 6/2007 | Nilsson et al. | |
| 7,491,708 B1 | 2/2009 | Platt et al. | |
| 7,638,623 B2 | 12/2009 | Nilsson et al. | |
| 7,700,763 B2 | 4/2010 | Leffler | |
| 7,893,252 B2 | 2/2011 | Platt et al. | |
| 8,092,825 B2 | 1/2012 | Jablonski | |
| 8,128,966 B2 | 3/2012 | Staples et al. | |
| 8,187,642 B1 | 5/2012 | Staples et al. | |
| 8,236,780 B2 * | 8/2012 | Platt et al. ...................... 514/54 |
| 8,409,635 B2 | 4/2013 | Staples et al. | |
| 8,420,133 B2 | 4/2013 | Staples et al. | |
| 2003/0004132 A1 | 1/2003 | Chang et al. | |
| 2003/0013682 A1 | 1/2003 | Banito et al. | |
| 2004/0023925 A1 | 2/2004 | Chang et al. | |
| 2004/0043962 A1 | 3/2004 | Chang et al. | |
| 2004/0121981 A1 | 6/2004 | Chang et al. | |
| 2004/0223971 A1 | 11/2004 | Chang et al. | |
| 2005/0008572 A1 | 1/2005 | Prokop et al. | |
| 2005/0239129 A1 | 10/2005 | Brady et al. | |
| 2006/0094688 A1 | 5/2006 | Tanaka et al. | |
| 2006/0211653 A1 | 9/2006 | Platt | |
| 2006/0225731 A1 | 10/2006 | Woortman et al. | |
| 2007/0258969 A1 | 11/2007 | Zomer et al. | |
| 2008/0089959 A1 | 4/2008 | Chang et al. | |
| 2008/0107622 A1 | 5/2008 | Platt | |
| 2010/0316640 A1 | 12/2010 | Sundaram et al. | |
| 2011/0046086 A1 | 2/2011 | Yun | |

(Continued)

FOREIGN PATENT DOCUMENTS

WO    WO2013/101314    7/2013

OTHER PUBLICATIONS

Banh et al. "Tumor galectin-1 mediates tumor growth and metastasis through regulation of T-cell apoptosis," Cancer Res. 71:4423-31 (2011).

(Continued)

*Primary Examiner* — Patrick Lewis
(74) *Attorney, Agent, or Firm* — Greenberg Traurig, LLP

(57) ABSTRACT

Methods and compositions of the invention relate to the treatment of diabetic nephropathy and associated disorders. In particular, the methods and compositions use a pharmaceutical-grade galactose-pronged carbohydrate or pharmaceutical compositions thereof alone or in combination with other therapeutic agents.

18 Claims, 3 Drawing Sheets
(3 of 3 Drawing Sheet(s) Filed in Color)

(56) References Cited

U.S. PATENT DOCUMENTS

| | | |
|---|---|---|
| 2012/0149658 A1 | 6/2012 | Staples et al. |
| 2012/0165277 A1 | 6/2012 | Leffler et al. |
| 2013/0243831 A1 | 9/2013 | Stpales et al. |

OTHER PUBLICATIONS

Barondes et al., "Galectins: a family of animal beta-galactoside-binding lectins [letter]," Cell. (76):597-598 (1994).

Barrow at al., "The role of galectins in colorectal cancer progression," Int. J. Cancer. 129: 1-8 (2011b).

Cay et al., "Review Immunohistochemical expression of galectin-3 in cancer: a review of the literature," Patoloji Derg. 28(1): 1-10 (2012).

Forsman et al., "Galectin 3 aggravates joint inflammation and destruction in antigen-induced arthritis," Arthritis Reum. 63: 445-454 (2011).

Godwin Avwioro, "Histochemical Uses of Haematoxylin—A Review," JPCS. 1: 24-34 (2011).

Kolatsi-Joannou et al., "Modified citrus pectin reduces galectin-3 expression and disease severity in experimental acute kidney injury," PLoS One. 6: e18683, doi:10.1371/journal.pone.0018683 (2011).

Lefranc et al., "Galectin-1 mediated biochemical controls of melanoma and glioma aggressive behavior," World J. Biol. Chem. 2: 193-201 (2011).

Liu et al., "Galectins in regulation of inflammation and immunity," In Galectins (ed. by Klyosov, A.A., Witzhak, Z.A., and Platt, D.), John Wiley & Sons, Hoboken, New Jersey, pp. 97-113 (2008).

López et al., "Gene expression profiling in lungs of chronic asthmatic mice treated with galectin-3: downregulation of inflammatory and regulatory genes," Mediators Inflamm., 823279. Epub Mar. 20, 2011 (2011).

Newlaczyl et al., "Galectin-3—a jack-of-all-trades in cancer," Cancer Lett. 313: 123-128 (2011).

Ohshima et al., "Galectin 3 and its binding protein in rheumatoid arthritis," Arthritis Rheum. 48: 2788-2795 (2003).

Sato et al., Galectins as danger signals in host-pathogen and host-tumor interactions: new members of the growing group of "Alarmins" In "Galectins," (Klyosov, et al eds.), John Wiley and Sons, 115-145 (2008).

Toussaint et al., "Galectin-1, a gene preferentially expressed at the tumor margin, promotes glioblastoma cell invasion," Mol Cancer. 11: 32. (2012).

Wang et al., "Nuclear and cytoplasmic localization of galectin-1 and galectin-3 and their roles in pre-mRNA splicing." In "Galectins" (Klyosov et al eds.), John Wiley and Sons, 87-95 (2008).

International Search Report mailed Dec. 6, 2013 in connection with PCT/US2013/64322.

\* cited by examiner

GALACTOSE-PRONGED CARBOHYDRATE COMPOUNDS FOR THE TREATMENT OF DIABETIC NEPHROPATHY AND ASSOCIATED DISORDERS

RELATED APPLICATION(S)

This application claims the benefit of and priority to U.S. Provisional Application Ser. No. 61/711,929, filed Oct. 10, 2012, the entire disclosure of which is incorporated herein by reference in its entirety.

FIELD OF THE INVENTION

Aspects of the invention relate to methods of treating diabetic nephropathy and associated disorders using a pharmaceutical-grade galactose-pronged polysaccharide, or pharmaceutical compositions thereof.

BACKGROUND OF THE INVENTION

Diabetic Nephropathy is a progressive kidney disease caused by angiopathy of capillaries in the kidney glomeruli. It is characterized pathologically as a diffuse glomerulosclerosis which results in proteinuria, nephrotic syndrome, progressive reduction in glomerular filtration rate, and results eventually in renal failure.

Diabetic nephropathy is due to longstanding diabetes mellitus, and is the major indication for dialysis in many Western countries.

While control of serum glucose level and control of blood pressure are effective in reducing the progression of diabetic nephropathy, renal failure remains a major health problem. Accordingly, there is a great need to provide therapies that are efficacious in preventing, slowing the progression, or reversing diabetic nephropathy.

SUMMARY OF THE INVENTION

Some aspects of the invention relate to a therapeutic formulation having a suitable or increased efficacy in the treatment of diabetic nephropathy. In some embodiments, the therapeutic formulation includes an effective dose of a galactose-pronged polysaccharide compound. In some embodiments, the therapeutic formulation can be administered alone or co-administered with an effective dose of a therapeutic agent in a mixture or regimen. The formulation may further include an additional therapeutic agent for the treatment of diabetic nephropathy or diabetes or excipients in which the formulation is in a powder form or in a liquid form.

In some embodiments, an effective dose of a galactose-containing polysaccharide can be administered in a formulation for oral administration. The formulation may include methods of physical alterations of the compound or additions of various agents that enhance the oral absorption of the galactose-containing polysaccharide.

In some embodiments, the compound is a galactose-containing polysaccharide and can be used in combination with a therapeutically effective amount of one or more other galectin inhibitor that may inhibit single galectin proteins or a set of galectin proteins. Galectin inhibitors can include, but are not limited to, small organic inhibitors of galectin, monoclonal antibodies, RNA inhibitors, small binding peptides, protein inhibitors or combinations thereof.

In some embodiments, the method of treating comprises the step of obtaining a pharmaceutical composition for parenteral or enteral administration comprising a galactose-pronged carbohydrate compound in an acceptable pharmaceutical carrier.

In some embodiments, the compound is a polysaccharide that may be chemically defined as galacto-rhamnogalacturonate, a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal). Other side chain minor constituents may include arabinose (Ara), xylose (Xyl), glucose (Glu), and fucose (Fuc).

In some embodiments, the compound is a galactose-pronged carbohydrate that may be chemically defined as a subtype of galacto-rhamnogalacturonate termed galactoarabino-rhamnogalacturonate, a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal) and 1,5apha L arabinose (Ara) residues. Other side chain minor constituents may include xylose (Xyl), glucose (Glu), and fucose (Fuc).

In some embodiments, the compound can be synthesized from natural pectin. Yet, in some embodiments, the compound can be a synthetic galactose-pronged compound.

In some embodiments, the compound can be synthesized from natural, highly branched, minimally processed and high methoxylated USP pectin which may come from any plant sources, including but not limited to, citrus fruits, apple, or beet.

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis by alkaline (pH 8 to 12) and acid (pH 1-5) or beta-elimination by peroxide or other chemistry or by suitable enzymatic hydrolysis and fractionation.

In some embodiments the compound can be produced by a process comprising depolymerization catabolized by targeted peroxidation cleavage of glycosidic bonds by ionized OH sup- generated from ascorbic acid and/or peroxide in presence or absence of additional reduced form of a transition metal ion, like Cu sup.++. at 1 to 100 mM. Other transition metals like Ca. sup.++ or Fe.sup.++ can also be used for this purpose.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas Chromatography-Mass Spectroscopy) and AELC-PAD (Anion Exchange Liquid Chromatography-Pulsed Amperometric Detector) methods.

In some embodiments, the molar percent of the 1,4-β-D-Gal and 1,5-α-L-Ara residues in the compound of the present invention can exceed 10% of the total molar carbohydrates with approximate ratio ranging from 1:1 to 3:1 respectively.

In some embodiments, the molar percent of 1,5-α-L-Ara residues in the compound of the present invention may be zero or only found in trace amounts of up to 1%.

In some embodiments, the compound is a polysaccharide chemically defined as galacto-rhamnogalacturonate or galactoarabino-rhamnogalacturonate, a branched heteropolymer with average molecular weight distribution of 2,000 to 80,000, or 20,000 to 70,000, or 5,000 to 55,000 Daltons, as determined by SEC-RI and/or the SEC-MALLS methods.

In some embodiments, the compound can be a highly soluble modified polysaccharide sufficiently reduced in molecular weight range, for example from about 2,000 to about 80,000 D, so as to be compatible with therapeutic formulations for pluralistic administration via routes including but not limited to intravenous, subcutaneous, intra-articular, inhaled, and oral.

In some embodiments, the galactose-pronged carbohydrate compound can comprise a galactomannan polysaccharide. In some embodiments, the compound is a galactomannan oligosaccharide consisting essentially of galactose and mannose residues and resulting from a sufficiently controlled depolymerization of galactomannan so as to result in a galactomannan polysaccharide composition with a defined average molecular weight.

In some embodiments, the galactomannan polysaccharide composition consists essentially of galactose and mannose residues and results from a sufficiently controlled depolymerization of galactomannan. In some embodiments, the composition comprises a homogenous galactomannan polysaccharide. In some embodiments, the galactomannan polysaccharide has an average weight of 4,000 to 60,000 D, as assayed by GPC-MALLS (galactomannan).

In some embodiments, the galactomannan polysaccharide composition has a ratio of mannose to galactose molecules in a range of 1:1 to 1:4.

In some embodiments, the galactomannan polysaccharide composition has a ratio of mannose to galactose molecules of 1.7:1.

In some embodiments, the galactomannan polysaccharide composition is produced by a process designed to generate a highly pure soluble and homogeneous oligomer with an average molecular weight in the range of about 48,000 Daltons, and mannose to galactose ratio in the range of about 1.7:1. In some embodiments, the product is in the form of a highly soluble oligomer of galactomannan (GM).

In some embodiments, the galactose-containing polysaccharide and other compounds described, are proposed as therapy alone or in combination with other agents in glomerulopathic diseases that are secondary to systemic diseases including but not limited to diabetic nephropathy, systemic lupus erythematosis, amyloidosis, Goodpasture's Syndrome, microscopic polyarthritis/polyangiitis, Wegeners granulomatosis, Henoch Schonlein purpura, and disorders associated with immune complex deposition in the kidney.

In some embodiments, the galactose-containing polysaccharide and other compounds described, are proposed as therapy alone or in combination with other agents in primary glomerulopathic diseases including but not limited to acute diffuse proliferative glomerulonephritis (post-streptococcal and non-streptococcal), rapidly progressive glomerulonephritis, chronic glomerulonephritis, membranous glomerulonephritis, minimal change disease, focal segmented glomerulosclerosis, membrane proliferative glomerulonephritis, and IgA nephropathy.

In some embodiments, the galactose-containing polysaccharide and other compounds described, are proposed as therapy alone or in combination with other agents in renal tubule-interstitial disorders or systemic disease that includes expansion and extracellular matrix deposition in the interstitial space which includes but is not limited to diabetic nephropathy, interstitial nephritis, and immunologic damage to the liver including but not limited to allograph rejection.

In some embodiments, a therapeutically effective dose can be evaluated by an effect on diabetic nephropathy that results in at least a 10% reduction in proteinuria or at least a 10% reduction in the rate of increase of proteinuria, including but not limited to albumin protein.

In some embodiments, a therapeutically effective dose can be evaluated by an effect on diabetic nephropathy that results in at least a 10% increase in glomerular filtration rate or at least a 10% reduction in the rate of decline of glomerular filtration rate, as measured by any standard method.

In some embodiments, a therapeutically effective dose can be evaluated by an effect on diabetic nephropathy that results in at least a 10% reduction of mesangial extracellular matrix or at least a 10% reduction in the rate of increase of mesangial extracellular matrix, as measured on histological sections of kidney.

In some embodiments, a therapeutically effective dose can be evaluated by an effect on diabetic nephropathy that results in at least a 5% reduction in the glomerular capillary basement membrane thickness, as measured on histological sections of kidney using either light or electron microscopy.

In some embodiments, a therapeutically effective dose can be evaluated by an effect on diabetic nephropathy that results in at least a 10% reduction in the fractional volume of the mesangium or at least a 10% reduction in the rate of increase of the fractional volume of the mesangium, as measured on histological sections of the kidney.

In some embodiments, a therapeutically effective dose can be evaluated by an effect on diabetic nephropathy that results in at least a 10% reduction in the interstitial tubular volume or at least a 10% reduction in the rate of increase in the interstitial volume, as measured on histological sections of the kidney.

In some embodiments, a therapeutically effective dose can be evaluated by an effect on diabetic nephropathy that results in at least a 10% reduction in the amount of collagen in the interstitial tubular space or at least a 10% reduction in the rate of increase of the collagen in the interstitial tubular space, as measured on histological sections of kidney.

In some embodiments, a therapeutically effective dose can be evaluated by an effect on diabetic nephropathy that results in a change of at least 10% in the level of the serum biomarkers of diabetic nephropathy. Such markers include but are not limited to inflammatory and hemodynamic cytokines, TNF-alpha, TGF-beta or IL-8, osteopontin, or a metabolic profile of serum components that is indicative of diabetic nephropathy presence or severity (including serum and urine markers). A profile of one or more of these cytokines, as measured by immunoassay or proteomic assessment by LC mass spec, may provide an assessment of activity of the disease and a marker to follow in therapy of the disease.

Some aspects of the invention relate to a method comprising obtaining a composition for parenteral or enteral administration comprising a galacto-rhamnogalacturonate in a pharmaceutical acceptable carrier, and administering to a subject in need thereof an effective dose of the composition. In some embodiments, the effective dose is equivalent to an animal dose of 0.1 mg/kg to 9.9 mg/kg and results in at least one of the following at least a 10% reduction in proteinuria or at least a 10% reduction in the rate of increase of proteinuria; at least a 10% increase in glomerular filtration rate or at least a 10% reduction in the rate of decline of glomerular filtration rate; at least a 10% reduction of mesangial extracellular matrix or at least a 10% reduction in the rate of increase of mesangial extracellular matrix; at least a 5% reduction in the glomerular capillary basement membrane thickness; at least a 10% reduction in the fractional volume of the mesangium or at least a 10% reduction in the rate of increase of the fractional volume of the mesangium; at least a 10% reduction in the interstitial tubular volume or at least a 10% reduction in the rate of increase in the interstitial volume; at least a 10% reduction in the amount of collagen in the interstitial tubular space or at least a 10% reduction in the rate of increase of the collagen in the interstitial tubular space; at least 10% change in the level of the serum biomarkers of diabetic nephropathy. In some embodiments, the subject in need thereof has at least one of the following: a primary glomerulopathic disease, a secondary glomerulopathic disease, and renal tubule-interstitial disorder. In some embodiments, the serum biomarkers of diabetic nephropathy comprise inflammatory and hemodynamic cytokines, TNF-alpha, TGF-beta or IL-8, osteopontin, or a metabolic profile of serum components indicative of diabetic nephropathy presence or severity. In some embodiments, the effective dose can range from 0.05 to 0.49 mg/kg.

In some embodiments, the galacto-rhamnogalacturonate comprises a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues.

In some embodiments, the galacto-rhamnogalacturonate comprises a 1,4-linked galacturonic acid (GalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues.

In some embodiments, the galacto-rhamnogalacturonate can further comprise xylose, glucose, fucose residues or combination thereof.

In some embodiments, the galacto-rhamnogalacturonate can have an average molecular weight distribution of 2,000 to 80,000, 20,000 to 70,000, or 5,000 to 55,000 Daltons, as determined by SEC-RI and/or the SEC-MALLS methods.

In some embodiments, the galacto-rhamnogalacturonate can be substantially free of 1,5-α-L-Ara residues.

In some embodiments, the composition further comprises one or more galectin inhibitors. In some embodiments, the galectin inhibitors can comprise small organic inhibitors of galectin, monoclonal antibodies, RNA inhibitors, small binding peptides, protein inhibitors or combinations thereof.

Some aspects of the invention relate to a method comprising obtaining a composition for parenteral or enteral administration comprising a galactoarabino-rhamnogalacturonate in a pharmaceutical acceptable carrier, and administering to a subject in need thereof an effective dose is equivalent to an animal dose of 0.1 mg/kg to 1.99 mg/kg of the composition. In some embodiments, the effective dose results in at least one of the following at least a 10% reduction in proteinuria or at least a 10% reduction in the rate of increase of proteinuria; at least a 10% increase in glomerular filtration rate or at least a 10% reduction in the rate of decline of glomerular filtration rate; at least a 10% reduction of mesangial extracellular matrix or at least a 10% reduction in the rate of increase of mesangial extracellular matrix; at least a 5% reduction in the glomerular capillary basement membrane thickness; at least a 10% reduction in the fractional volume of the mesangium or at least a 10% reduction in the rate of increase of the fractional volume of the mesangium; at least a 10% reduction in the interstitial tubular volume or at least a 10% reduction in the rate of increase in the interstitial volume; at least a 10% reduction in the amount of collagen in the interstitial tubular space or at least a 10% reduction in the rate of increase of the collagen in the interstitial tubular space; at least 10% change in the level of the serum biomarkers of diabetic nephropathy. In some embodiments, the subject in need thereof has at least one of the following: a primary glomerulopathic disease, a secondary glomerulopathic disease, and renal tubule-interstitial disorder. In some embodiments, the serum biomarkers of diabetic nephropathy comprise inflammatory and hemodynamic cytokines, TNF-alpha, TGF-beta or IL-8, osteopontin, or a metabolic profile of serum components indicative of diabetic nephropathy presence or severity. In some embodiments, the effective dose can range from 0.05 to 0.19 mg/kg.

In some embodiments, the galacto-rhamnogalacturonate is a galactoarabino-rhamnogalacturonate, comprising a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof. In some embodiments, the molar percent of the 1,4-β-D-Gal, 1,5-α-L-Ara residues and combination thereof is at least 8% of the total molar carbohydrates. In some embodiments, the 1,4-β-D-Gal and 1,5-α-L-Ara residues can be present at a ratio ranging from 1:1 to 3:1. In some embodiments, the galactoarabino-rhamnogalacturonate can have an average molecular weight distribution of 2,000 to 80,000, 20,000 to 70,000, or 5,000 to 55,000 Daltons, as determined by SEC-RI and/or the SEC-MALLS methods. In some embodiments, the galactoarabino-rhamnogalacturonate can have a degree of methoxylation ranging from 40% to 70%. In some embodiments, the galactoarabino-rhamnogalacturonate can have a methyl galacturonate plus galacturonic acid ratio to galactose ranging from 4:1 to 7:1.

Aspects of the invention relate to a composition comprising an effective dose equivalent to an animal dose of 0.1 mg/kg to 1.99 mg/kg of a galactoarabino-rhamnogalacturonate in an acceptable pharmaceutical carrier for use in treatment of diabetic nephropathy, wherein the galactoarabino-rhamnogalacturonate comprises a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof. In some embodiments, the effective dose can range from 0.05 to 0.19 mg/kg.

Aspects of the invention relate to a composition comprising an effective dose equivalent to an animal dose of 0.1 mg/kg to 9.99 mg/kg of a galacto-rhamnogalacturonate in an acceptable pharmaceutical carrier for use in treatment of diabetic nephropathy, wherein the galacto-rhamnogalacturonate comprises a 1,4-linked galacturonic acid (GalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues. In some embodiments, the effective dose can range from 0.05 to 0.49 mg/kg.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be further explained with reference to the attached drawings, wherein like structures are referred to by like numerals throughout the several views. The drawings shown are not necessarily to scale, with emphasis instead generally being placed upon illustrating the principles of the present invention.

DETAILED DESCRIPTION OF THE INVENTION

Figure 1:
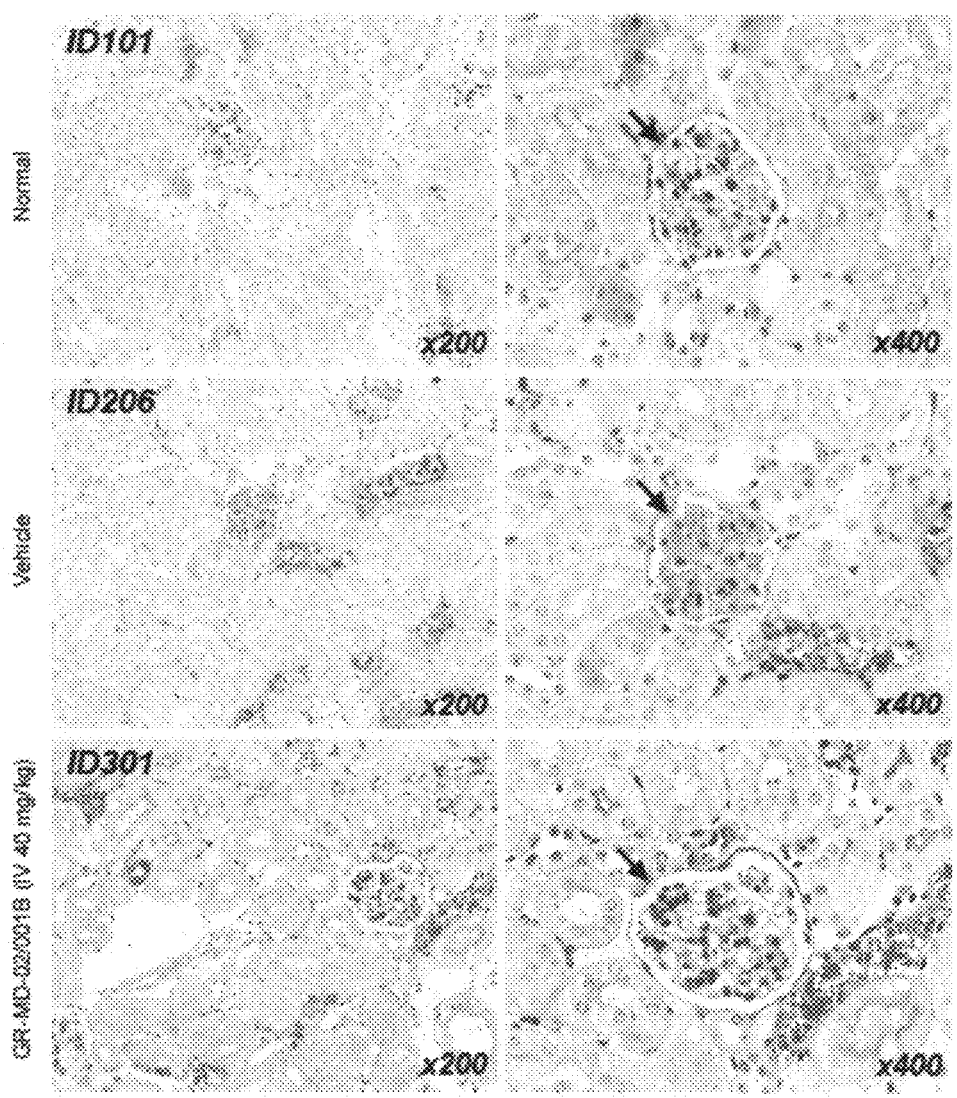
FIG. 1 shows histological sections of mouse kidneys stained with Periodic Acid Schiff (PAS) reagent. Shown are low (×200) and high magnification (×400) pictures of the three experimental groups: 1) Normal mouse; 2) Diabetic mice treated with vehicle (phosphate buffered saline, treatment control); and 3) Diabetic mice treated with GR-MD-02/001 B (IV 40 mg/kg). The arrows point to a glomerulus.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Unless otherwise specified, all percentages expressed herein are weight/weight.

Between 20% and 40% of patients with diabetes (Type I and Type II) ultimately develop diabetic nephropathy. Diabetic nephropathy also known as Kimmelstiel-Wilson syndrome, or nodular diabetic glomerulosclerosis and intercapillary glomerulonephritis, is a progressive kidney disease caused by angiopathy of capillaries in the kidney glomeruli. Diabetic nephropathy is the leading cause of chronic kidney disease in the United States and other Western societies, responsible for 30-40% of all end-stage renal disease in the United States. It is also one of the most significant long-term complications in terms of morbidity and mortality for individual patients with diabetes.

Diabetic nephropathy is a clinical syndrome characterized by the following:
1) Persistent albuminuria (>300 mg/d or >200 μg/min), 2) Progressive decline in the glomerular filtration rate (GFR), 3) Elevated arterial blood pressure.

Diabetic nephropathy is generally diagnosed after a routine urinalysis and screening for microalbuminuria in the setting of diabetes.

Patients may have physical findings associated with long-standing diabetes mellitus, such as, hypertension, peripheral vascular disease, evidence of diabetic neuropathy in the form of decreased fine sensations and diminished tendon reflex, evidence of fourth heart sound during cardiac auscultation, or non-healing skin ulcers/osteomyelitis. Almost all patients with nephropathy and Type I diabetes demonstrate signs of diabetic microvascular disease, such as retinopathy and neuropathy.

Patients with diabetic nephropathy have a progressive and inexorable reduction in glomerular filtration rate. Patients with diabetic nephropathy with Type I or Type II diabetes have a decline in glomerular filtration rate from about 9.6 to 12 ml/min/year to about 5.4 to 7.2 ml/min/year, respectively While there is good evidence suggesting that early treatment delays or prevents the onset of diabetic nephropathy or diabetic kidney disease, it remains a major health problem. Accordingly, there is a need for treatment that can prevent, delay progression, or cause regression of the disease.

The classic kidney pathology in diabetic nephropathy is nodular glomerulosclerosis. Three major histologic changes occur in the glomeruli of persons with diabetic nephropathy: 1) mesangial cell expansion and increased matrix production and/or glycosylation of matrix proteins; 2) thickening of the glomerular basement membrane (GBM) occurring after mesangial cell and matrix expansion; 3) glomerular sclerosis. These different histologic patterns appear to have similar prognostic significance.

The key change in diabetic glomerulopathy is the augmentation of extracellular matrix. The earliest morphologic abnormality in diabetic nephropathy is the thickening of the glomerular basement membrane and expansion of the mesangium due to the accumulation of extracellular matrix.

As the glomerular pathology progresses, there is an increasing pathological change in the interstitium between kidney tubules which includes increased deposition of extracellular matrix material and collagen.

Histological findings show an increase of deposition of extracellular matrix material and collagen in the solid spaces of the glomerulus, most frequently observed as coarse branching of solid (positive periodic-acid Schiff reaction (PAS)) material, but there are also large acellular accumulations, or nodules (Kimmelstiel-Wilson lesions/nodules).

The severity of diabetic glomerulopathy can be estimated by the thickness of the peripheral basement membrane and mesangium and matrix expressed as a fraction of appropriate spaces (e.g., volume fraction of mesangium/glomerulus, matrix/mesangium, or matrix/glomerulus).

Immunofluorescence microscopy may reveal deposition of albumin, immunoglobulins, fibrin, and other plasma proteins along the glomerular basement membrane in a linear pattern most likely as a result of exudation from the blood vessels.

In advanced disease, electron microscopy shows that the mesangial regions occupy a large proportion of the glomerulus, with prominent matrix content. Further, the basement membrane in the capillary walls (i.e., the peripheral basement membrane) is thicker than normal.

In addition to the glomerular pathology, diabetic nephropathy results in increased matrix material in the tubular interstitial spaces of the kidney. The severity of the interstitial disease can be determined by measuring the amount of matrix material between renal tubular cells including but not limited to collagen type I, collagen type IV, hyaluronic acid, hyaluronan, and proteoglycans.

The underlying pathophysiology leading to the pathological lesions is not completely understood, but can include products of advanced glycation and oxidative stress. It is believed that the development of diabetic nephropathy is linked to hyperglycemia. Glucose can reacts nonenzymatically with proteins to form Schiff base and Amadori products and to advanced glycation end-products (AGEs), which are believed to play a central role in the progression of diabetic nephropathy The pathophysiology can also involve a variety of inflammatory and cytotoxic cytokines including, but not limited to transforming growth factor β1, angiotensin II, and nitric oxide.

Some aspects of the invention relate to methods for treating (e.g., controlling, relieving, ameliorating, alleviating, or slowing the progression of) or methods for preventing (e.g., delaying the onset of or reducing the risk of developing) one or more diseases, disorders, or conditions in which galectins are involved, in a subject in need thereof are featured. In some aspects, the methods include administering to the subject an effective amount of a galactose-pronged carbohydrate compound, or a composition comprising the galactose-pronged carbohydrate compound, to a subject having diabetic nephropathy.

As used herein, the term "effective dose" refers to the amount of a compound that, alone or in combination with an amount of a therapeutic agent, when administered as a parental, subcutaneous, inhaled, intra-articular, ocular, or oral formulation or to an animal or human with diabetic nephropathy or associated disease results in reduction in disease activity, as defined below in various embodiments. For example, the term "effective dose" means the amount of galactose-pronged carbohydrate or other agent in combination with galactose-pronged carbohydrate that, when administered as a parental dose or in an oral formulation to an animal or human with diabetic nephropathy that results in at least one of the following: at least a 10% reduction in proteinuria (including but not limited to albumin protein), at least a 10% increase in glomerular filtration rate, at least a 10% reduction of mesangial extracellular matrix, at least a 10% reduction in the glomerular capillary basement membrane thickness, at least a 10% reduction in the fractional volume of the mesangium, at least a 10% reduction in the interstitial tubular volume, and/or at least a 10% reduction in the amount of collagen in the interstitial tubular space.

The term "pharmaceutically acceptable carrier" refers to a carrier or adjuvant that may be administered to a subject (e.g., a patient), together with a compound of this invention, and which does not destroy the pharmacological activity thereof and is nontoxic when administered in doses sufficient to deliver a therapeutic amount or an effective mount of the compound. For example, the term pharmaceutically acceptable carrier can refer to any and all solvents, dispersion media, e.g., human albumin or cross-linked gelatin polypeptides, coatings, antibacterial and antifungal compounds, isotonic, e.g., sodium chloride or sodium glutamate, and absorption delaying compounds, and the like that are physiologically compatible. The use of such media and compounds for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

The term "efficacy" refers in some embodiments to demonstrating an improvement in the pathology, disease manifestations or clinical findings of diabetic nephropathy or other primary or secondary glomerulonephropathies.

In some embodiments, the method of treating comprises the step of obtaining a composition for parenteral or enteral administration comprising a galactose-pronged carbohydrate compound in an acceptable pharmaceutical carrier.

In some embodiments, the compound is a polysaccharide that may be chemically defined as galacto-rhamnogalacturonate, a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal). Other side chain minor constituents may include arabinose (Ara), xylose (Xyl), glucose (Glu), and fucose (Fuc).

In some embodiments, the compound is a galactose-pronged carbohydrate that may be chemically defined as a subtype of galacto-rhamnogalacturonate termed galactoarabino-rhamnogalacturonate, a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-β-D-galactose (Gal) and 1,5apha L arabinose (Ara) residues. Other side chain minor constituents may include xylose (Xyl), glucose (Glu), and fucose (Fuc).

In some embodiments, the molar percent of the 1,4-β-D-Gal and 1,5-α-L-Ara residues in the compound of the present invention can exceed 10% of the total molar carbohydrates with approximate ratio ranging from 1:1 to 3:1 respectively.

In some embodiments, the molar percent of 1,5-α-L-Ara residues in the compound of the present invention may be zero or only found in trace amounts of up to 1%.

[[In some embodiments, the compound is a galactose-pronged carbohydrate that may be chemically defined as a galactoarabino-rhamnogalacturonan compound comprising a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof.

In some embodiments, the compound can have a degree of methoxylation ranging from 40% to 70% of the maximum of 87%. In some embodiments, the compound has a methyl galacturonate to galacturonic acid ratio ranging from 2:1 to 1:2. In some embodiments, the compound has a methyl galacturonate plus galacturonic acid ratio to galactose ranging from 4:1 to 7:1

In some embodiments, the oligomer of 1,4-β-D-galactose residues, 1,5-α-L-arabinose residues or combinations thereof represents at least 8 molar percent of the total carbohydrate molar content. In some embodiments, the 1,4-β-D-galactose and 1,5-α-L-arabinose residues are present in a 2:1 or a 3:1 ratio.

In some embodiments, the compound is a polysaccharide chemically defined as galacto-rhamnogalacturonate or galactoarabino-rhamnogalacturonate, a branched heteropolymer with average molecular weight distribution of 2,000 to 80,000, or 20,000 to 70,000, or 5,000 to 55,000 Daltons, as determined by SEC-RI and/or the SEC-MALLS methods.

In some embodiments, the compound can be a highly soluble modified polysaccharide sufficiently reduced in molecular weight range, for example from about 2,000 to about 80,000 D, so as to be compatible with therapeutic formulations for pluralistic administration via routes including but not limited to intravenous, subcutaneous, intra-articular, inhaled, and oral.

In some embodiments the galacto-rhamnogalacturonate compound can be produced by the method described in U.S. Ser. No. 8,236,780 and PCT/US12/55311, which are incorporated herein by reference in their entirety for all purposes.

In some embodiments, the compound can be synthesized from natural, highly branched, minimally processed and high methoxylated USP pectin which may come from any plant sources, including but not limited to, citrus fruits, apple, or beet.

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas chromatography-mass spectroscopy) and AELC-PAD (anion exchange liquid chromatography-pulsed amperometric detector) methods.

In some embodiments, the compound can be synthesized under a sufficiently controlled and specific hydrolysis by alkaline (pH 8 to 12) and acid (pH 1-5) or beta-elimination by peroxide or other chemistry or by suitable enzymatic hydrolysis and fractionation.

In some embodiments the compound can be produced by a process comprising depolymerization catabolized by targeted peroxidation cleavage of glycosidic bonds by ionized OH sup- generated from ascorbic acid and/or peroxide in presence or absence of additional reduced form of a transition metal ion, like Cu sup.++. at 1 to 100 mM. Other transition metals like Ca. sup.++ or Fe.sup.++ can also be used for this purpose.

As used herein, the term "depolymerization" refers to partial, selective or complete hydrolysis of the polysaccharide backbone occurring, for example, when the polysaccharide is treated chemically resulting in fragments of reduced size when compared with the original polysaccharide.

In some embodiments, the depolymerized compound can be exposed to pH of between 8 to 10, for 10 to 30 minutes at temperature of 2° C. to 60° C. to initiate controlled limited demethoxylation to generate a depolymerized compound with a degree of methoxylation of 40 to 70 percent in comparison to initial levels of maximum 87% and can be referred to as middle-methoxylated compound. Complete methoxylation of galacturonic acid is considered to be approximately DE 87%.

In some embodiments, the depolymerized composition can be exposed to multiple washes of hot acidic alcohol (e.g at temperatures ranging from 30° C. to 80° C.) to remove any residual endotoxin, copper and heavy metals, agricultural contaminants and other impurities.

In some embodiments, soluble chemically altered galacto-rhamnogalacturonates are prepared by modifying naturally occurring polymers to reduce the molecular weight for the desired range, reducing the alkylated group (de-methoxylation or deacetylation). Prior to chemical modification, the natural polysaccharides may have a molecular weight range of between about 40,000-1,000,000 D with multiple branches of saccharides, for example, branches comprised of 1 to 20 monosaccharides of glucose, arabinose, galactose etc, and these branches may be connected to the backbone via neutral monosaccharides such as rhamnose. These molecules may further include a single or chain of uronic acid saccharide backbone that may be esterified from as little as about 2% to as much as about 70%. The multiple branches themselves may have multiple branches of saccharides, the multiple branches optionally including neutral saccharides and neutral saccharide derivatives creating mainly hydrophobic entities.

In some embodiments, the galacto-rhamnogalacturonate composition may be produced by various treatments, including heat, high or low pH, various forms of molecular weight exclusion filtration (or combinations of these methods) using raw pectin material from any plant source. For example, raw pectin material can be from apple, citrus, or beet pectin, some of which are available commercially as USP pectin material.

In some embodiments, the compound comprises a modified pectin. Several composition of carbohydrate compounds and process for manufacturing the same have been described. See U.S. Pat. Nos. 6,573,245, 6,645,946, 6,914,055, 6,982,255, 7,012,068, 7.491,708 and 7,893,252, the disclosure of each of theses patents are incorporated herein by reference in their entirety for all purposes.

In some embodiments, the galacto-rhamnogalacturonate composition is produced as described in U.S. Pat. No. 8,128,966 and U.S. application No. US 2012-0149658, the disclosure of each which are incorporated expressly by reference in its entirety for all purposes In some embodiments, the galactose-pronged carbohydrate composition is produced as described in U.S. Provisional Applications Ser. Nos 61/704,174 and 61/693,978, the disclosure of each of theses patents are incorporated herein by reference in their entirety for all purposes.

In some embodiments, the compound falls within the general class comprising a substantially demethoxylated polygalacturonic acid backbone having rhamnose residues pendent therefrom. It is believed that in materials of this type, the terminal galactose units pendent from the backbone bind to galectin proteins. The remaining bulk of the molecule can potentiate the compound's action in moderating immune system response. While not wishing to be bound by speculation, the remaining bulk of the molecule may either interact with remaining portions of the galectin protein and/or may prolong the binding of the sugar portion thereto.

In some embodiments, the compound can comprise a galactomannan polysaccharide. In some embodiments, the compound is a galactomannan oligosaccharide consisting essentially of galactose and mannose residues and resulting from a sufficiently controlled depolymerization of galactomannan so as to result in a galactomannan polysaccharide composition with a defined average molecular weight.

Galactomannan can be obtained from a variety of natural sources such as plants and microbial sources. The polysaccharide can also be synthetically made. Galactomannan can be derived from carob gum (*Ceratonia siliqua*), guar gum (*Cyamopsis tetragonoloba*), and honey locust (*Gleditsia triacanthos*), are examples of commercial available galactomannans. The polysaccharides include, but are not limited to, galactomannans available from a number of plant and microbial sources. For example, the galactomannan can be a derivative of Guar gum from seeds of *Cyamopsis tetragonoloba*. Yet in other embodiments, the galactomannan can be a derivative of *Gleditsia triacanthos, medicago falcate, Trigonella Foenum-graecum* and microbial like *Ceratonia siliqua Xanthomonas campestris*, yeast and mold galactomannan, Arabinogalactan (from *Larix occidentalis*), Rhamnogalacturonan (from potato), Carrageenan (from Eucheuma Seaweed), and the Locust Bean Gum (from *Ceratonia siliqua*.

As used herein, the term "backbone" means the major chain of a polysaccharide, or the chain originating from the major chain of a starting polysaccharide, having saccharide moieties sequentially linked by either alpha or beta glycosidic bonds. A backbone may comprise additional monosaccharide moieties connected thereto at various positions along the sequential chain.

In some embodiments, the galactomannan polysaccharide composition consists essentially of galactose and mannose residues and resulting from a sufficiently controlled depolymerization of galactomannan so as to result in a homogenous galactomannan polysaccharide. In some embodiments, the galactomannan polysaccharide has an average weight of 4,000 to 60,000 D, as assayed by GPC-MALLS (galactomannan).

In some embodiments, the galactomannan polysaccharide composition has a ratio of mannose to galactose molecules in a range of 1:1 to 1:4.

In some embodiments, the galactomannan polysaccharide composition has a ratio of mannose to galactose molecules of 1.7:1.

In some embodiments, the galactomannan polysaccharide composition is produced as described in U.S. Pat. No. 7,893,252 incorporated expressly by reference in its entirety for all purposes. The process is designed to generate a highly pure soluble and homogeneous oligomer with an average molecular weight in the range of about 48,000 Daltons, and mannose to galactose ratio in the range of about 1.7:1. The process incorporates four major phases: controlled depolymerization to produce the desired galactomannan oligomer and three purification steps, removal of insoluble impurities, removal of water soluble impurities, removal of organic soluble impurities, and finally freeze drying to generate a pure and stable form of galactomannan powder. In some embodiments, the product is in the form of a highly soluble oligomer of galactomannan (GM).

Galactomannan can be packaged and delivered as a sterile concentrated solution in a single use vial, while bulk galactomannan can be produced and stored as powder. The process described herein is for both bulk drug and final drug product. The galactomannan drug product can be combined and administered together with a therapeutically effective amount of a therapeutic agent to form the active ingredients of a pharmaceutical preparation. In some embodiments, the drug product can contain normal saline for infusion (about 0.9 M sodium chloride in water) and has a pH of about 6.5.

While the foregoing discussion has been primarily directed to therapeutic materials based upon modified pectins and galactomannan, it is to be understood that the present invention is not so limited. In accord with the general principles of the present invention, any member of the broad class of compounds which can interact with and block galectins may be employed. These materials, in an embodiment, comprise carbohydrate materials, since such materials are low in toxicity and exhibit strong interaction with galectins or exhibit a strong anti-inflammatory effect. Modified pectin materials comprise one particularly group of carbohydrate materials. Likewise, synthetic and semi-synthetic analogs thereof such as polygalacturonic acid materials may be similarly employed.

Yet another class of materials of the present invention comprises molecules which have a first portion, which is typically a carbohydrate, and which is capable of binding to galectins, joined to a second portion which inactivates or otherwise moderates the activity of a protein. This second portion need not be a carbohydrate and can comprise a material which cross links or otherwise denatures the segment of protein comprising an active portion of the galectin protein, or an active portion of another protein which interacts with the galectin. Such materials include active species such as sulfur or other chalcogen elements alone or in combination such as thiols, sulfhydryls and the like. Other active species may comprise cyano groups, thiocyanates, alkylating agents, aldehydes and the like. Some active species may be proteins including but not limited to monoclonal antibodies.

In some embodiments, the method comprises the steps of obtaining a galactose-pronged carbohydrate compound for parenteral or enteral administration in an acceptable pharmaceutical carrier.

In some embodiments, the method comprises the steps of obtaining a galactose-pronged carbohydrate compound for parenteral or enteral administration comprising a chemically modified, and or derivatives of, disaccharide or oligosaccharide that has at least one galactose as starting chemical structure including but not limited to galactopyranosides or 3-triazolyl-galactosides.

In some embodiments, the chemically modified disaccharide or oligosaccharide composition is produced as described in U.S. Pat. No. 6,444,655 incorporated expressly by reference in its entirety for all purposes.

In some embodiments, the chemically modified disaccharide or oligosaccharide composition is produced as described in U.S. Pat. No. 8,092,825 incorporated herein by reference in its entirety for all purposes.

In some embodiments, the chemically modified disaccharide or oligosaccharide composition is produced as described in U.S. Pat. No. 7,700,763 incorporated herein by reference in its entirety for all purposes.

In some embodiments, the chemically modified disaccharide or oligosaccharide composition is produced as described in U.S. Pat. No. 7,638,623 incorporated herein by reference in its entirety for all purposes.

In some embodiments, the chemically modified disaccharide or oligosaccharide composition is produced as described in U.S. Pat. No. 7,230,096 incorporated herein by reference in its entirety for all purposes.

In some embodiments, the galactose-pronged compound may be synthesized as described in U.S. Provisional Applications Nos. 61/704,174 and 61/693,978, incorporated herein by reference in their entirety for all purposes.

In some embodiments, the galactose-pronged carbohydrate compound can be used in combination with a therapeutically effective amount of a therapeutic agent. For example, the galactose-pronged carbohydrate compound can be used in combination with a therapeutically effective amount of a conventional therapeutic agent for diabetic nephropathy.

In some embodiment, the galactose-pronged carbohydrate compound can be used in admixture. "Admixture" means more than one component mixed together to form a combination. For purposes of the present invention, "admixture" means the mixture of two or more compounds at any time prior or subsequent to, or concomitant with, administration.

Some aspects of the invention relate to a diabetic nephropathy therapeutic formulation having a suitable or increased efficacy in the treatment of diabetic nephropathy. In some embodiments, the diabetic nephropathy therapeutic formulation includes an effective dose of a galactose-pronged polysaccharide. In some embodiments, the diabetic nephropathy therapeutic formulation can be administered alone or co-administered with an effective dose of a therapeutic agent in a mixture or regimen. The formulation may further include an additional diabetic nephropathy or diabetes therapeutic agent or excipients in which the formulation is in a powder form or in a liquid form.

In another embodiment, an effective dose of a galactose-containing polysaccharide can be administered in a formulation for oral administration. The formulation may include methods of physical alterations of the compound or additions of various agents that enhance the oral absorption of the galactose-containing polysaccharide. Alterations of the compound may include but are not limited to linkage to a hydrophobic moiety such as but not limited to an aliphatic group. Additions to the formulation that may enhance absorption may include, but not be limited to, agents that increase the permeability of the intestinal barrier.

In some embodiments, the compound is a galactose-containing polysaccharide and can be used in combination with a therapeutically effective amount of one or more other galectin inhibitor that may inhibit single galectin proteins or a set of galectin proteins. Galectin inhibitors can include but are not limited to small organic inhibitors of galectin, monoclonal antibodies, RNA inhibitors, small binding peptides, protein inhibitors or combinations thereof.

In some embodiments, the galactose-containing polysaccharide and other compounds described, are proposed as therapy alone or in combination with other compounds listed above, for human diabetic nephropathy as a method of preventing, slowing progression of, or ameliorating or reversing the disease.

In some embodiments, the galactose-containing polysaccharide and other compounds described, are proposed as therapy alone or in combination with other compounds listed above in primary glomerulopathic diseases including but not limited to acute diffuse proliferative glomerulonephritis (post-streptococcal and non-streptococcal), rapidly progressive glomerulonephritis, chronic glomerulonephritis, membranous glomerulonephritis, minimal change disease, focal segmented glomerulosclerosis, membrane proliferative glomerulonephritis, and IgA nephropathy.

In some embodiments, the galactose-containing polysaccharide and other compounds described, are proposed as therapy alone or in combination with other compounds listed above in glomerulopathic diseases that are secondary to systemic diseases including but not limited to diabetic nephropathy, systemic lupus erythematosis, amyloidosis, Goodpasture's Syndrome, microscopic polyarthritis/polyangiitis, Wegeners granulomatosis, Henoch Schonlein purpura, and disorders associated with immune complex deposition in the kidney.

In some embodiments, the galactose-containing polysaccharide and other compounds described, are proposed as therapy alone or in combination with other compounds listed above in renal tubule-interstitial disorders or systemic disease that includes expansion and extracellular matrix deposition in the interstitial space which includes but is not limited to diabetic nephropathy, interstitial nephritis, and immunologic damage to the liver including but not limited to allograph rejection.

In some embodiments, an effective dose of galactose-containing polysaccharide can be administered via a variety of routes including, parenteral via an intravenous infusion given as repeated bolus infusions or constant infusion, intradermal injection, subcutaneously given as repeated bolus injection or constant infusion, or oral administration.

An effective parental dose (given intravenously, intraperitoneally, or subcutaneously) of galactose containing polysaccharide to an experimental animal is within the range of 0.1 mg/kg up to 160 mg/kg body weight, or 1 mg/kg, or 10 mg/kg, or 30 mg/kg, or 60 mg/kg, or 90 mg/kg, or 120 mg/kg body weight. In some embodiments, the effective parental dose (given intravenously, intraperitoneally, or subcutaneously) of galactose containing polysaccharide to an experimental animal is in the range of 0.1 mg/kg to 1 mg/kg, 0.1 to 1.5 mg/kg, 0.1 mg/kg to 1.9 mg/kg. In some embodiments, the effective parental dose (given intravenously, intraperitoneally, or subcutaneously) of galactose containing polysaccharide to an experimental animal is in the range of 0.1 mg/kg to 3 mg/kg, 0.1 mg/kg to 4 mg/kg, 0.1 mg/kg to 5 mg/kg, 0.1 mg/kg to 6 mg/kg, 0.1 mg/kg to 7 mg/kg, 0.1 mg/kg to 8 mg/kg, 0.1 mg/kg to 9 mg/kg, or 0.1 mg/kg to 9.9 mg/kg. In some embodiments, the effective parental dose (given intravenously, intraperitoneally, or subcutaneously) of galactose containing polysaccharide to an experimental animal is less than 10 mg/kg or is less than 2 mg/kg.

In some embodiments, the effective parental dose (given intravenously, intraperitoneally, or subcutaneously) of galacto-rhamnogalacturonate to an experimental animal can be 0.1 mg/kg, 0.5 mg/kg, 1 mg/kg, 2, mg/kg, 5 mg/kg, 6 mg/kg, 7 mg/kg, 8 mg/kg, 9 mg/kg or 9.99 mg/kg. In some embodiments, the effective parental dose (given intravenously, intraperitoneally, or subcutaneously) of galacto-rhamnogalacturonate to an experimental animal can be in the range of 0.1 to 9.99 mg/kg, 0.2 to 9.99 mg/kg, 0.3 to 9.99 mg/kg, 0.4 to 9.99 mg/kg, 0.5 to 9.99 mg/kg, 1 to 9.99 mg/kg, 2 to 9.99 mg/kg, 3 to 9.99 mg/kg, 4 to 9.99 mg/kg, 5 to 9.99 mg/kg, 6 to 9.99mg/kg, 7 to 9.99 mg/kg, 8 to 9.99 mg/kg, 9 to 9.99 mg/kg, 0.1 to 0.2 mg/kg, 1 to 2 mg/kg, 2 to 3 mg/kg, 3 to 4 mg/kg, 4 to 5 mg/kg, 5 to 6 mg/kg, 6 to 7 mg/kg, 7 to 8 mg/kg, 8 to 9 mg/kg.

In some embodiments, the effective parental dose (given intravenously, intraperitoneally, or subcutaneously) of galactoarabino-rhamnogalacturonate to an experimental animal can be 0.1 mg/kg, 0.2 mg/kg, 0. 40 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3, mg/kg 1.4 mg/kg, 1.5, mg/kg, 1. 5 mg/kg, 1.6 mg/kg, 1.7 mg/kg, 1.8 mg/kg, 1.9 mg/kg, or 1.99 mg/kg. In some embodiments, the effective parental dose (given intravenously, intraperitoneally, or subcutaneously) of galactoarabino-rhamnogalacturonate to an experimental animal can be in the range of 0. 1 mg/kg to 0.2 mg/kg, 0.2 to 0.3 mg/kg, 0.3 mg/kg to 0.4mg/kg, 0.4 to 0.5 mg/kg, 0.5 mg/kg to 0.6 mg/kg, 0.6 mg/kg, to 0.7 mg/kg, 0.7 to 0.8 mg/kg, 0.8 to 0.9 mg/kg, 0.9 mg/kg to 1 mg/kg, 1 to 1.1 mg/kg, 1.1 to 1. 2 mg/kg, 1.2 to 1. 3 mg/kg, 1.3 mg/kg to 1.4 mg/kg, 1.4 mg/kg to 1.5 mg/kg, 1.5 to 1.6 mg/kg, 1.6 to 1.7 mg/kg, 1.7 to 1.9 mg/kg, or 1.9 to 1.99 mg/kg.

An effective parenteral dose (given intravenously, intraperitoneally, or subcutaneously) of galactose containing polysaccharide to an experimental animal can be administered three times weekly, twice weekly, once weekly, once every two weeks, once monthly, or as a constant infusion.

In some embodiments, an effective parenteral dose of galactose containing polysaccharide to a human is defined as the equivalent to the animal dose that gives the same systemic exposure in humans as in animals. The equivalency of systemic exposure is defined as the same area under the curve ($AUC_{infinity}$) performed as part of a pharmacokinetic parameter analysis. For example, the human equivalent dose to an animal dose would be the dose in humans that gave the same systemic exposure, or AUC, as found in the animals at that dose. In some embodiments, the experimental animal model is the mouse.

In some embodiments, the effective parental dose (given intravenously, intraperitoneally, or subcutaneously) of galacto-rhamnogalacturonate is equivalent to animal dose in the range of 00.1 to 9.99 mg/kg, 0.2 to 9.99 mg/kg, 0.3 to 9.99 mg/kg, 0.4 to 9.99 mg/kg, 0.5 to 9.99 mg/kg, 1 to 9.99 mg/kg, 2 to 9.99 mg/kg, 3 to 9.99 mg/kg, 4 to 9.99 mg/kg, 5 to 9.99 mg/kg, 6 to 9.99mg/kg, 7 to 9.99 mg/kg, 8 to 9.99 mg/kg, 9 to 9.99 mg/kg, 0.1 to 0.2 mg/kg, 1 to 2 mg/kg, 2 to 3 mg/kg, 3 to 4 mg/kg, 4 to 5 mg/kg, 5 to 6 mg/kg, 6 to 7 mg/kg, 7 to 8 mg/kg, 8 to 9 mg/kg. In some embodiments, the effective parental dose (given intravenously, intraperitoneally, or subcutaneously) of galactoarabino-rhamnogalacturonate is equivalent to animal dose in the range of 0.1 mg/kg to 0.2 mg/kg, 0.2 to 0.3 mg/kg, 0.3 mg/kg to 0.4 mg/kg, 0.4 to 0.5 mg/kg, 0.5 mg/kg to 0.6 mg/kg, 0.6 mg/kg, to 0.7 mg/kg, 0.7 to 0.8 mg/kg, 0.8 to 0.9 mg/kg, 0.9 mg/kg to 1 mg/kg, 1 to 1.1 mg/kg, 1.1 to 1.2 mg/kg, 1.2 to 1.3 mg/kg, 1.3 mg/kg to 1.4 mg/kg, 1.4 mg/kg to 1.5 mg/kg, 1.5 to 1.6 mg/kg, 1.6 to 1.7 mg/kg, 1.7 to 1.9 mg/kg, or 1.9 to 1.99 mg/kg.

An effective parental dose (given intravenously or subcutaneously) of galactose containing polysaccharide to a human subject is within the range of 0.05 mg/kg up to 25 mg/kg body weight, or 1 mg/kg, or 2 mg/kg, or 5 mg/kg, or 7.5 mg/kg, or 10 mg/kg body weight, or 15 mg/kg body weight. In some embodiments, an effective parental dose is in the range of (given intravenously or subcutaneously) of galactose containing polysaccharide to a human subject is within the range of 0.05 mg/kg to 0.1 mg/kg, of 0.05 mg/kg to 0.19 mg/kg, of 0.05 mg/kg to 0.3 mg/kg, of 0.05 mg/kg to 0.4 mg/kg or of 0.05 mg/kg to 0.49 mg/kg. In some embodiments, an effective parental dose (given intravenously or subcutaneously) of galactose containing polysaccharide to a human subject is less than 0.5 mg/kg or is less than 0.2 mg/kg. For example, the effective parental dose (given intravenously, intraperitoneally, or subcutaneously) of galactose containing polysaccharide to an experimental animal can be 0.05 mg/kg, 0.1 mg/kg, 0.19 mg/kg. In some embodiments, the effective parental dose (given intravenously, intraperitoneally, or subcutaneously) of galactose containing polysaccharide to an experimental animal can be 0.05 mg/kg, 0.1 mg/kg, 0.2 mg/kg 0.3 mg/kg, 0.4 mg/kg, or 0.49 mg/kg.

In some embodiments, the effective parental dose (given intravenously, intraperitoneally, or subcutaneously) of galacto-rhamnogalacturonate can be within the range of 0.05 mg/kg to 0.1 mg/kg, of 0.05 mg/kg to 0.2 mg/kg, of 0.05 mg/kg to 0.3 mg/kg, of 0.05 mg/kg to 0.4 mg/kg or of 0.05 mg/kg to 0.49 mg/kg, 0.1 mg/kg to 0.2 mg/kg, 0.2 mg/kg to 0.3 mg/kg, 0.3 mg/kg to 0.4 mg/kg, 0.4 mg/kg to 0.49 mg/kg, 0.2 mg/kg to 0.49 mg/kg, 0.3 to mg/kg to 0.49 mg/kg.

In some embodiments, the effective parental dose (given intravenously, intraperitoneally, or subcutaneously) of galactoarabino-rhamnogalacturonate can be 0.05 mg/kg to 0.1 mg/kg, 0.05 mg/kg to 0.06 mg/kg, 0.05 mg/kg to 0.07 mg/kg, 0.05 mg/kg to 0.08 mg/kg, 0.05 mg/kg to 0.09 mg/kg, 0.05 mg/kg to 0.11 mg/kg, 0.05 mg/kg to 0.12 mg/kg, 0.05 mg/kg to 0.13 mg/kg, 0.05 mg/kg to 0.14 mg/kg, 0.05 mg/kg to 0.15 mg/kg, 0.05 mg/kg to 0.16 mg/kg, 0.05 mg/kg to 0.17 mg/kg, 0.05 mg/kg to 0.18 mg/kg, 0.1 to 0.19 mg/kg.

An effective parenteral dose (given intravenously or subcutaneously) of galactose containing polysaccharide to a human subject can be administered three times weekly, twice weekly, once weekly, once every two weeks, once monthly, or as a constant infusion.

In some embodiments, diabetic nephropathy can be modeled in animals including but not limited to mice, rats, swine, cynomolgus monkey. In these animals, diabetes can be induced by a variety of methods, including but not limited to treatment with an islet cell toxin (including but not limited to high-dose and low-dose streptozotocin) and/or providing a high fat diet.

In some embodiments, diabetic nephropathy can be modeled in mouse genetic models. Such models include, but are not limited to the NOD mouse, the Insulin-2 Akita mouse, the db/db mouse, the Ob/ob mouse, mice with the agouti mutation, the NZO mouse, or various mice with monogenetic mutations or transgenic mice including but not limited to the genes for apolipoprotein E, endothelial nitric oxide synthase, mutations that lead to increased AGE, and GLUT1 or inbred mice with strain dependent development of diabetes.

In some embodiments, a therapeutically effective dose can be evaluated by an effect on diabetic nephropathy that results in at least a 10% reduction in proteinuria or at least a 10% reduction in the rate of increase of proteinuria, including but not limited to albumin protein.

In some embodiments, a therapeutically effective dose can be evaluated by an effect on diabetic nephropathy that results in at least a 10% increase in glomerular filtration rate or at least a 10% reduction in the rate of decline of glomerular filtration rate, as measured by any standard method.

In some embodiments, a therapeutically effective dose can be evaluated by an effect on diabetic nephropathy that results in at least a 10% reduction of mesangial extracellular matrix or at least a 10% reduction in the rate of increase of mesangial extracellular matrix, as measured on histological sections of kidney.

In some embodiments, a therapeutically effective dose can be evaluated by an effect on diabetic nephropathy that results in at least a 5% reduction in the glomerular capillary basement membrane thickness, as measured on histological sections of kidney using either light or electron microscopy.

In some embodiments, a therapeutically effective dose can be evaluated by an effect on diabetic nephropathy that results in at least a 10% reduction in the fractional volume of the mesangium or at least a 10% reduction in the rate of increase of the fractional volume of the mesangium, as measured on histological sections of the kidney.

In some embodiments, a therapeutically effective dose can be evaluated by an effect on diabetic nephropathy that results in at least a 10% reduction in the interstitial tubular volume or at least a 10% reduction in the rate of increase in the interstitial volume, as measured on histological sections of the kidney.

In some embodiments, a therapeutically effective dose can be evaluated by an effect on diabetic nephropathy that results in at least a 10% reduction in the amount of collagen in the interstitial tubular space or at least a 10% reduction in the rate of increase of the collagen in the interstitial tubular space, as measured on histological sections of kidney.

In some embodiments, a therapeutically effective dose can be evaluated by an effect on diabetic nephropathy that results in a change of at least 10% in the level of the serum biomarkers of diabetic nephropathy. Such markers include but are not limited to inflammatory and hemodynamic cytokines, TNF-alpha, TGF-beta or IL-8, osteopontin, or a metabolic profile of serum components that is indicative of diabetic nephropathy presence or severity (including serum and urine markers). A profile of one or more of these cytokines, as measured by immunoassay or proteomic assessment by LC mass spec, may provide an assessment of activity of the disease and a marker to follow in therapy of the disease.

In some embodiments, a therapeutically effective dose can be evaluated by an effect on diabetic nephropathy that results in a reduction in clinical complications of chronic renal insufficiency or failure such as, for example, the need for kidney replacement therapy including dialysis and renal transplantation.

Example 1

Method of Manufacturing Galactose-Pronged Carbohydrate Compound

The following is an illustrative example of the production of a therapeutic polysaccharide that is not meant to limit the invention. In this case, the galactose-pronged carbohydrate compound is galactoarabino-rhamnogalacturonate produced has been labeled GR-MD-02/001B in this application.

Apple pectin USP HM (50 kg) was dissolved and heated in water to 35-85° C. 1 M HCl or NaOH was added in order to pH-adjust the solution to pH 5-7 and mixed well. The mixing was continued for 2 hours at the 35-85° C. set point. 1M NaOH or HCl was added as needed to readjust pH to between 5 and 7. Solution was cooled to 30° C. At 30° C., pH was adjusted to between 5 and 7.

$CuSO_4$ is added to the pH-adjusted pectin solution so as to result in a final 1 mM $CuSO_4$ concentration. The 1 mM $CuSO_4$ solution was mixed for 30 minutes at a temperature of between 10° C. and 30° C.

At the conclusion of the 30 minute, 1 mM $CuSO_4$ mixing step, 50 grams sodium ascorbate was added (amount was pre-calibrated to achieve the desired MW) and mixed for 5 to 20 minutes. $H_2O_2$ was added start with 0.02 and up to 1.0 moles/kg pectin (pre-calibrated for initial starting pectin MW) and the $H_2O_2$ concentration was maintained for 4 hours (using quantitative test, Sigma, St-Louis) while the solution pH was maintained between 4 and 7.

5M NaOH was added to the solution so as to result in a solution pH of between 8 and 10. The pH-adjusted solution was mixed for 10-30 minutes. Concentrated HCL was then added to the pH-adjusted solution to adjust the pH of the solution to between 4 and 5. The solution, once adjusted to pH between 4 and 5 can be kept mixing for 2 to 24 hours between 2° C. and 8° C.

Solution was then heated to 80° C. for 30-180 minutes and 1-5 kg of Filter-Aid was added (Celite) to the solution, and the solution with added Celite was stirred for 30 minutes and then filtered. The solids resulting from the filtration were discarded.

The filtrate was concentrated 1.5-3x under vacuum, and then pH-adjusted to between 3 and 5. Hot ethanol or isopropanol was added on a 50% weight. The mixture was stirred 1-2 hours to precipitate product, and the mixture was then filtered. The filtrate was discarded, leaving a white to off-white precipitate.

Cold 96% EtOH was added to the solution and the resulting slurry was then stirred for 30 minutes. The solution was filtered and the filtrate was discarded. The 96% EtOH slurry step was repeated, followed by a final filtration and recovery of the white to off-white precipitate.

Example 2

Method of Treatment of a Mouse Model of Diabetic Nephropathy

The experimental model used in this example is the mouse in which diabetes was induced and a high fat diet was administered. Diabetes was induced immediately following birth with a single injection of streptozotocin. Four weeks later the mice were started on a high fat diet.

Diabetic mice were treated either with vehicle (phosphate buffered saline) or GR-MD-02/001B given intravenously in a dose of 40 mg/kg three times weekly for four weeks total. There were eight (8) mice in each group. Two normal mice were also utilized as a comparison group.

Blood glucose levels were markedly elevated in both the vehicle control and GR-MD-02/001B groups with no statistical differences between the groups. The normal blood glucose in mice was approximately 100 mg/dL and the average in the diabetic animals was between 700 and 800 mg/dL, hence demonstrating that all animals had overt diabetes.

The diabetic mice had clear histological evidence of diabetic nephropathy as shown in pictures of PAS stained kidney sections in FIG. 1. The arrow in each group shows a glomerulus, the structure that is most affected in this disease. In the vehicle treated control animals there is a clear increase in mesangial basement membrane material (the pink extracellular matrix) over the normal animals. In comparison, the mice treated with GR-MD-02/001B showed a marked decrease in the mesangial extracellular matrix material as compared to the vehicle treated control animals.

Figure 2:
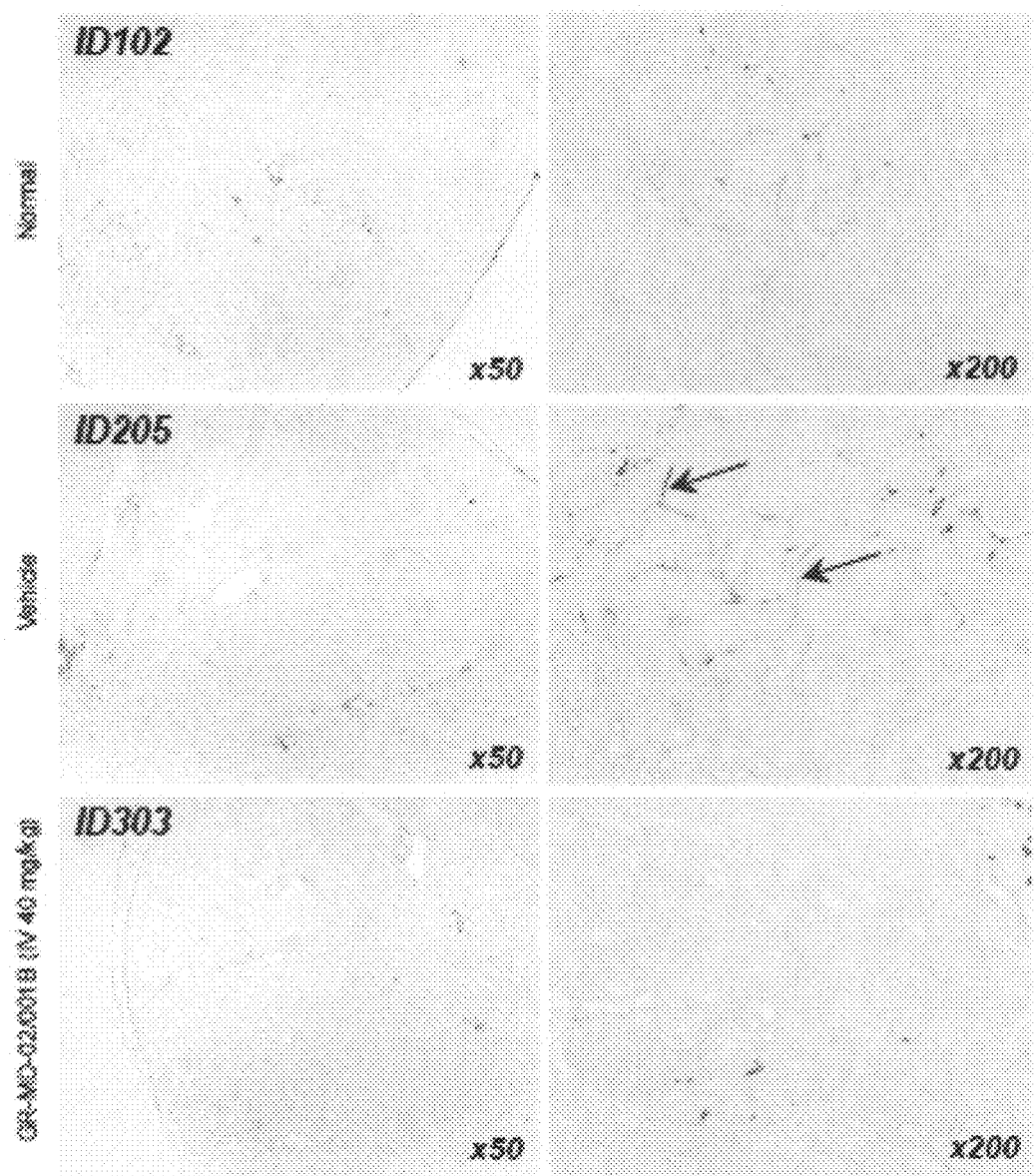
FIG. 2 shows histological sections of mouse kidneys stained with pico Sirius red reagent. Shown are low (×50) and high magnification (×200) pictures of the three experimental groups: 1) Normal mouse; 2) Diabetic mice treated with vehicle (phosphate buffered saline, treatment control); and 3) Diabetic mice treated with GR-MD-02/001 B (IV 40 mg/kg). The arrows point to a stained strand that indicates the presence of collagen type.

FIG. 2 shows kidney sections stained with Sirius red reagent which specifically stains collagen type I fibers. Sirius red reagent is used as a stain to evaluate the increase in extracellular matrix material in the interstitium between tubular cells. Minimal red staining is seen in the normal animals. However, there is an increase in staining seen in the vehicle treated control animals. This is represented by linear regions of red staining in a "chicken wire" configuration which indicates that there is increased collagen in the interstitial spaces between renal tubules. Following treatment with GR-MD-02/001B, there is a marked reduction in Sirius red staining, indicating that treatment reduced interstitial collagen.

Figure 3:
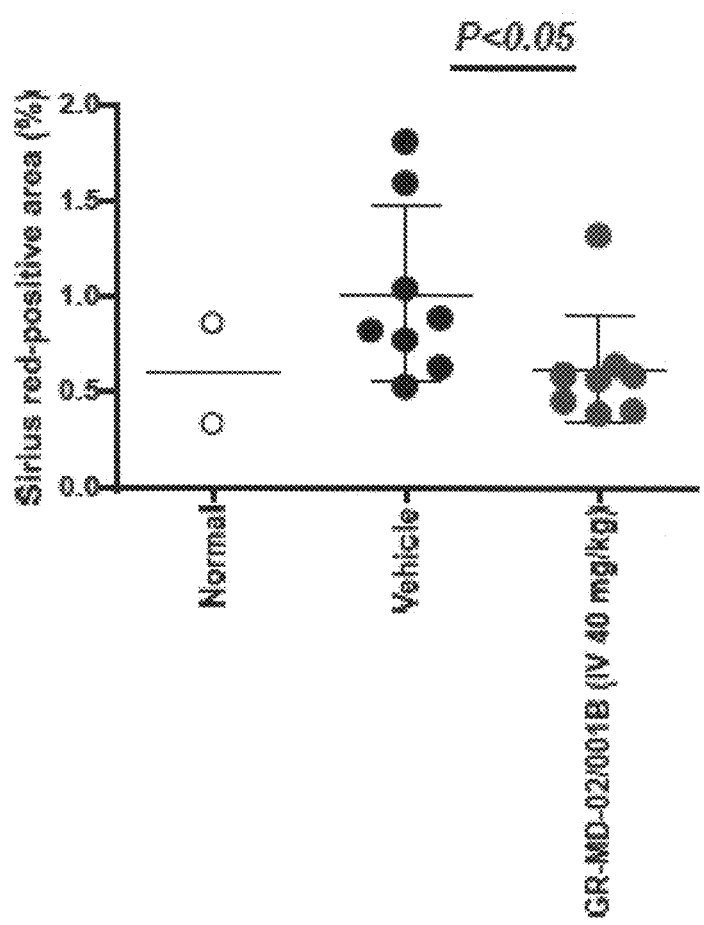
FIG. 3 shows the results of digital morphometry of mouse kidneys stained with pico Sirius red reagent in order to quantitate the percent Sirius red staining. Statistical comparisons of the percent Sirius red staining shown for the three experimental groups: 1) Normal mouse; 2) Diabetic mice treated with vehicle (phosphate buffered saline, treatment control); and 3) Diabetic mice treated with GR-MD-02/001 B (IV 40 mg/kg).

FIG. 3 shows a statistical comparison of the percent of Sirius red staining among the experimental groups. Thirty two (32) separate slides from each group were blindly evaluated by quantitative digital morphometry for the percent staining with Sirius red. The figure shows that vehicle treated control animals has an increase in Sirius red staining when compared to normal animals indicating that there was deposition of collagen in the interstitial spaces between tubules in the diabetic model. Treatment with GR-MD-02/001B resulted in a statistically significant decrease in Sirius red staining as compared to vehicle treated controls, with levels nearly the same as normal mice.

This example demonstrated that the mouse model of diabetes used exhibits sine-qua-non pathological changes of diabetic nephropathy. Moreover, contrary to a number of other models, it seems to recapitulate what is seen in human diabetic nephropathy in that it exhibits a glomerunephropathy and tubular interstitial expansion.

This example further showed that one of the many galactose-pronged carbohydrate compounds described in this invention, GR-MD-02/001B, had a therapeutic effect on the pathological manifestations of diabetic nephropathy in this mouse model. GR-MD02/001B reduced the mesangial expansion of extracellular matrix and reduced the deposition of matrix, as exemplified by collagen, in the tubular interstitial space.

The results of this example suggest that galactose-pronged carbohydrate compounds may be effective in the treatment of human diabetic nephropathy.

It is understood that the examples and embodiments described herein are for illustrative purposes only and that various modifications of changes in light thereof are to be included within the spirit and purview of this application and scope of the appended claims. All publication, patents and patent applications cited herein are hereby incorporated by reference in their entirety for all purposes.

The invention claimed is:
1. A method comprising:
   a. obtaining a composition for parenteral or enteral administration comprising a galacto-rhamnogalacturonate in a pharmaceutical acceptable carrier, and
   b. administering to a subject in need thereof an effective dose of the composition that results in at least one of the following:

at least a 10% reduction in proteinuria or at least a 10% reduction in the rate of increase of proteinuria;

at least a 10% increase in glomerular filtration rate or at least a 10% reduction in the rate of decline of glomerular filtration rate;

at least a 10% reduction of mesangial extracellular matrix or at least a 10% reduction in the rate of increase of mesangial extracellular matrix;

at least a 5% reduction in the glomerular capillary basement membrane thickness;

at least a 10% reduction in the fractional volume of the mesangium or at least a 10% reduction in the rate of increase of the fractional volume of the mesangium;

at least a 10% reduction in the interstitial tubular volume or at least a 10% reduction in the rate of increase in the interstitial tubular volume;

at least a 10% reduction in the amount of collagen in the interstitial tubular space or at least a 10% reduction in the rate of increase of the collagen in the interstitial tubular space;

at least 10% change in the level of the serum biomarkers of diabetic nephropathy;

wherein the subject in need thereof has at least one of the following: a primary glomerulopathic disease, a secondary glomerulopathic disease, and renal tubule-interstitial disorder, and wherein the effective dose is equivalent to an animal dose of 0.1 mg/kg to 9.99 mg/kg.

2. The method of claim 1 wherein the galacto-rhamnogalacturonate comprises a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues.

3. The method of claim 1 wherein the galacto-rhamnogalacturonate comprises a 1,4-linked galacturonic acid (GalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues.

4. The method of claim 1 wherein the galacto-rhamnogalacturonate further comprises xylose, glucose, fucose residues or combination thereof.

5. The method of claim 1 wherein the galacto-rhamnogalacturonate has an average molecular weight distribution of 2,000 to 80,000, 20,000 to 70,000, or 5,000 to 55,000 Daltons, as determined by SEC-RI and/or the SEC-MALLS methods.

6. The method of claim 1 wherein the galacto-rhamnogalacturonate is substantially free of 1,5-α-L-Ara residues.

7. The method of claim 1 wherein the serum biomarkers of diabetic nephropathy comprise inflammatory and hemodynamic cytokines, TNF-alpha, TGF-beta or IL-8, osteopontin, or a metabolic profile of serum components indicative of diabetic nephropathy presence or severity.

8. The method of claim 1 wherein the composition further comprises one or more galectin inhibitors.

9. The method of claim 8 wherein the galectin inhibitors comprise small organic inhibitors of galectin, monoclonal antibodies, RNA inhibitors, small binding peptides, protein inhibitors or combinations thereof.

10. The method of claim 1 wherein the effective dose ranges from 0.05 to 0.49 mg/kg.

11. A method comprising:
a. obtaining a composition for parenteral or enteral administration comprising a galactoarabino-rhamnogalacturonate in a pharmaceutical acceptable carrier, and
b. administering to a subject in need thereof an effective dose of the composition that results in at least one of the following:

at least a 10% reduction in proteinuria or at least a 10% reduction in the rate of increase of proteinuria;

at least a 10% increase in glomerular filtration rate or at least a 10% reduction in the rate of decline of glomerular filtration rate;

at least a 10% reduction of mesangial extracellular matrix or at least a 10% reduction in the rate of increase of mesangial extracellular matrix;

at least a 5% reduction in the glomerular capillary basement membrane thickness;

at least a 10% reduction in the fractional volume of the mesangium or at least a 10% reduction in the rate of increase of the fractional volume of the mesangium;

at least a 10% reduction in the interstitial tubular volume or at least a 10% reduction in the rate of increase in the interstitial tubular volume;

at least a 10% reduction in the amount of collagen in the interstitial tubular space or at least a 10% reduction in the rate of increase of the collagen in the interstitial tubular space;

at least 10% change in the level of the serum biomarkers of diabetic nephropathy;

wherein the subject in need thereof has at least one of the following: a primary glomerulopathic disease, a secondary glomerulopathic disease, and renal tubule-interstitial disorder, and wherein the effective dose is equivalent to an animal dose of 0.1 mg/kg to 1.99 mg/kg.

12. The method of claim 11 wherein the galactoarabino-rhamnogalacturonate comprises a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof.

13. The method of claim 11 wherein the molar percent of the 1,4-β-D-Gal, 1,5-α-L-Ara residues and combination thereof is at least 8% of the total molar carbohydrates.

14. The method of claim 11 wherein the 1,4-β-D-Gal and 1,5-α-L-Ara residues are present at a ratio ranging from 1:1 to 3:1.

15. The method of claim 11 wherein the galactoarabino-rhamnogalacturonate has an average molecular weight distribution of 2,000 to 80,000, 20,000 to 70,000, or 5,000 to 55,000 Daltons, as determined by SEC-RI and/or the SEC-MALLS methods.

16. The method of claim 11 wherein the galactoarabino-rhamnogalacturonate has a degree of methoxylation ranging from 40% to 70%.

17. The method of claim 11 wherein the galactoarabino-rhamnogalacturonate has a methyl galacturonate plus galacturonic acid ratio to galactose ranging from 4:1 to 7:1.

18. The method of claim 12 wherein the effective dose ranges from 0.05 to 0.19 mg/kg.

* * * * *